(12) United States Patent
Hung et al.

(10) Patent No.: US 6,359,089 B2
(45) Date of Patent: Mar. 19, 2002

(54) FLUOROVINYL ETHER CURE SITE MONOMERS AND FLUOROELASTOMER COPOLYMER COMPOSITIONS THEREOF

(75) Inventors: Ming-Hong Hung; Walter Werner Schmiegel, both of Wilmington, DE (US)

(73) Assignee: DuPont Dow Elastomers, L.L.C., Wilmington, DE (US)

( * ) Notice: Subject to any disclaimer, the term of this patent is extended or adjusted under 35 U.S.C. 154(b) by 0 days.

(21) Appl. No.: 09/815,137

(22) Filed: Mar. 22, 2001

Related U.S. Application Data

(60) Provisional application No. 60/198,351, filed on Apr. 19, 2000.

(51) Int. Cl.$^7$ .......................... C08L 27/12; C08L 27/16; C08L 27/18; C08L 27/20

(52) U.S. Cl. ..................... 526/247; 525/384; 526/250; 526/253; 526/254; 526/255; 568/615

(58) Field of Search ................. 526/247, 255, 526/250, 253, 254; 525/384; 568/615

(56) References Cited

U.S. PATENT DOCUMENTS

| | | | |
|---|---|---|---|
| 4,532,366 A | 7/1985 | Siegemund | 568/615 |
| 4,694,045 A | 9/1987 | Moore | |
| 4,758,618 A | 7/1988 | Ito | 524/430 |
| 4,982,009 A | 1/1991 | Hung | |
| 5,214,106 A | 5/1993 | Carlson et al. | |

*Primary Examiner*—Fred Zitomer

(57) ABSTRACT

Disclosed herein is a novel class of fluorovinyl ether monomers which are useful as cure site monomers in fluoroelastomers, a process for the preparation of these fluorovinyl ether monomers, and fluoroelastomer copolymer compositions that contain copolymerized units of these fluorovinyl ether monomers.

11 Claims, No Drawings

FLUOROVINYL ETHER CURE SITE MONOMERS AND FLUOROELASTOMER COPOLYMER COMPOSITIONS THEREOF

CROSS-REFERENCE TO RELATED APPLICATIONS

This application claims the benefit of U.S. Provisional Application No. 60/198,351 filed Apr. 19, 2000.

FIELD OF THE INVENTION

This invention relates to a novel class of fluorovinyl ether monomers which are useful as cure site monomers in fluoroelastomers, a process for the preparation of these fluorovinyl ether monomers and to curable fluoroelastomer copolymers having copolymerized units of these fluorovinyl ether monomers.

BACKGROUND OF THE INVENTION

Elastomeric fluoropolymers (i.e. fluoroelastomers) exhibit excellent resistance to the effects of heat, weather, oil, solvents and chemicals. Such materials are commercially available and are most commonly either dipolymers of vinylidene fluoride ($VF_2$) with hexafluoropropylene (HFP) or terpolymers of $VF_2$, HFP, and tetrafluoroethylene (TFE). While these di- and terpolymers have many desirable properties, including low compression set and excellent processability, their low temperature flexibility is not adequate for all applications, nor is their resistance to attack by alkaline solvents.

It is known that incorporation of perfluorinated ether monomer units into vinylidene fluoride elastomers improves low temperature properties, i.e. cured articles made from these polymers seal well at low temperatures. For example, Carlson, in U.S. Pat. No. 5,214,106 discloses that when perfluoro(methyl vinyl) ether (PMVE) is substituted for HFP, the resultant $VF_2$/PMVE/TFE copolymers have glass transition temperature ($T_g$) values which are 10°–20° C. lower than those of the corresponding $VF_2$/HFP/TFE copolymers. $T_g$ is often used as an indicator of low temperature flexibility because polymers having low glass transition temperatures maintain elastomeric properties at low temperatures.

Other common fluoroelastomers include the copolymers of TFE with one or more hydrocarbon olefins such as ethylene or propylene, and, optionally $VF_2$ (for example U.S. Pat. No. 4,758,618). These copolymers are generally more resistant to attack by alkaline solutions than other types of fluoroelastomers. The copolymers may also contain a perfluoro(alkyl vinyl) ether (PAVE) in order to impart good low temperature sealing properties (U.S. Pat. No. 4,694,045).

Many of the fluoroelastomers listed above require incorporation of a cure site monomer into their polymer chains in order to crosslink efficiently. Without such a cure site monomer, the fluoroelastomer may not react at all with curing agents, it may only partially react, or reaction may be too slow for use on a commercial scale. Seals made from poorly crosslinked elastomers often fail sooner than might otherwise be expected. Unfortunately, disadvantages are associated with many of the cure site monomers in use today. For example, monomers which contain reactive bromine or iodine atoms can release byproducts during the curing reaction that are harmful to the environment. Other cure site monomers (e.g. those which contain double bonds at both ends of the molecule) may be so reactive that they disrupt polymerization of the fluoroelastomer by altering the polymerization rate, terminating polymerization, or by causing undesirable chain branching, or even gelation to occur. Lastly, incorporation of a cure site monomer into a fluoroelastomer polymer chain may negatively impact the properties of the fluoroelastomer (both physical properties and chemical resistance).

There thus exists a need in the art for cure site monomers which are environmentally friendly, do not disrupt polymerization and which do not detract from the properties of the fluoroelastomer.

SUMMARY OF THE INVENTION

The present invention is directed to a fluorovinyl ether monomer of the formula $CF_3CHFCF_2$—$(O)_n$—$(CH_2)_m$—$(CF_2)_p$—$R_f$—$OCF$=$CF_2$, wherein $R_f$ is a $C_1$–$C_8$ perfluoroalkyl group or a $C_1$–$C_8$ perfluoroalkoxy group, n is 0 or 1, m is an integer from 1 to 3, and p is an integer from 1 to 4.

The present invention is also directed to a process for the preparation of the above fluorovinyl ether. The process comprises the steps of A. chlorinating an hydroxy vinyl ether compound of the formula HO—$(CH_2)_m$—$(CF_2)_p$—$R_f$—$OCF$=$CF_2$ to produce a chlorinated hydroxy ether of the formula HO—$(CH_2)_m$—$(CF_2)_p$—$R_f$—$OCFCl$—$CF_2Cl$;

B. condensing said chlorinated hydroxy ether with hexafluoropropene to produce a chorinated ether of the formula $CF_3CHFCF_2$—$(O)_n$—$(CH_2)_m$—$(CF_2)_p$—$R_f$—$OCFCl$—$CF_2Cl$; and C. dechlorinating said chlorinated ether to produce a fluorinated vinyl ether of the formula $CF_3CHFCF_2$—$(O)_n$—$(CH_2)_m$—$(CF_2)_p$—$R_f$—$OCF$=$CF_2$.

The present invention is also directed to a fluoroelastomer composition comprising A. copolymerized units of a first monomer, said first monomer being a fluoroolefin selected from the group consisting of vinylidene fluoride and tetrafluoroethylene;

B. copolymerized units of a second monomer, different from said first monomer, said second monomer selected from the group consisting of i) fluoroolefins, ii) hydrocarbon olefins, iii) perfluoro(alkyl vinyl)ethers and iv) perfluoro(alkoxy vinyl) ethers, and C. copolymerized units of a fluorinated vinyl ether cure site monomer of the formula $CF_3CHFCF_2$—$(O)_n$—$(CH_2)_m$—$(CF_2)_p$—$R_f$— $OCF$=$CF_2$, wherein $R_f$ is a $C_1$–$C_8$ perfluoroalkyl group or a $C_1$–$C_8$ perfluoroalkoxy (group, n is 0 or 1, m is an integer from 1 to 3, and p is an integer from 1 to 4.

The present invention is also directed to a polyhydroxylic curable composition of the above fluoroelastomer.

DETAILED DESCRIPTION OF THE INVENTION

The fluoroelastomers utilized in the curable compositions of the present invention are copolymers capable of undergoing crosslinking reactions with polyhydroxylic compounds to form cured elastomeric compositions that exhibit excellent physical properties and chemical resistance. Furthermore, the cure site monomers employed in the fluoroelastomers of this invention do not adversely affect the polymerization process, nor do byproducts of the curing reaction pose an environmental concern.

The fluoroelastomers of this invention comprise copolymerized units of A) a first monomer which is a fluoroolefin selected from the group consisting of vinylidine fluoride and tetrafluoroethylene B) a second monomer, which is not the same as the first monomer, and which is selected from the group consisting of fluoroolefins, hydrocarbon olefins, perfluoro(alkyl vinyl)ethers and perfluoro(alkoxy vinyl) ethers; and C) a fluorovinyl ether cure site monomer of the formula $CF_3CHFCF_2\!-\!(O)_n\!-\!(CH_2)_m\!-\!(CF_2)_p\!-\!R_f\!-\!OCF\!=\!CF_2$, wherein $R_f$ is a $C_1\!-\!C_8$ perfluoroalkyl group or a $C_1\!-\!C_8$ perfluoroalkoxy group, n is 0 or 1, m is an integer from 1 to 3, and p is an integer from 1 to 4.

Optionally, the fluoroelastomers of this invention may further comprise copolymerized units of at least one additional monomer, different from said first, second and cure site monomers. The additional monomer or monomers may be selected from the group consisting of perfluoro(alkyl vinyl) ethers, perfluoro(alkoxy vinyl) ethers, fluoroolefins and hydrocarbon olefins.

In addition, the fluoroelastomer copolymers of this invention may optionally contain up to about 1 wt. % iodine bound to polymer chain ends, the iodine being introduced via use of an iodine-containing chain transfer agent during polymerization.

Examples of fluoroolefin monomers useful as the second monomer and as the optional additional monomer in the fluoroelastomers of this invention include, but are not limited to vinylidene fluoride ($VF_2$), tetrafluoroethylene (TFE), chlorotrifluoroethylene (CTFE), hexafluoropropylene (HFP), pentafluoropropylene, vinyl fluoride and the like.

Hydrocarbon olefin monomers which may be employed as the second monomer and as the optional additional monomer in fluoroelastomers of this invention contain no fluorine atoms. Examples of such hydrocarbon olefins include, but are not limited to ethylene (E), propylene (P), butylene -1 and isobutylene.

Perfluoro(alkyl vinyl) ethers suitable for use as comonomers include those of the formula

$$CF_2\!=\!CFO(R_fO)_n(R_{f'}O)_mR_f \quad\quad\quad (I)$$

where $R_f$ and $R_{f'}$ are different linear or branched perfluoroalkylene groups of 2–6 carbon atoms, m and n are independently 0–10, and $R_f$ is a perfluoroalkyly group of 1–6 carbon atoms.

A preferred class of PAVE includes compositions of the formula

$$CF_2\!=\!CFO(CF_2CFXO)_nR_f \quad\quad\quad (II)$$

where X is F or $CF_3$, n is 0–5, and $R_f$ is a perfluoroalkyl group of 1–6 carbon atoms. A most preferred class of PAVE includes those ethers wherein n is 0 or 1 and $R_f$ contains 1–3 carbon atoms. Examples of such perfluorinated ethers include perfluoro(methyl vinyl) ether and perfluoro(propyl vinyl) ether. Other useful monomers include compounds of the formula

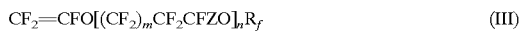
$$CF_2\!=\!CFO[(CF_2)_mCF_2CFZO]_nR_f \quad\quad\quad (III)$$

where $R_f$ is a perfluoroalkyl group having 1–6 carbon atoms m=0 or 1, n=0–5, and Z=F or $CF_3$.

Preferred members of this class are those in which $R_f$ is $C_3F_7$, m=0, and n=1.

Additional perfluoro(alkyl vinyl) ether monomers include compounds of the formula

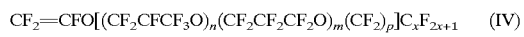
$$CF_2\!=\!CFO[(CF_2CFCF_3O)_n(CF_2CF_2CF_2O)_m(CF_2)_p]C_xF_{2x+1} \quad\quad\quad (IV)$$

where m and n independently=1–10, p=0–3, and x=1–5. Preferred members of this class include compounds where n=0–1, m=0–1, and x=1.

Examples of useful perfluoro(alkoxy vinyl) ethers include

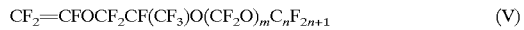
$$CF_2\!=\!CFOCF_2CF(CF_3)O(CF_2O)_mC_nF_{2n+1} \quad\quad\quad (V)$$

where n=1–5, m=1–3, and where, preferably, n=1.

Mixtures of perfluoro(alkyl vinyl) ethers and perfluoro (alkoxy vinyl) ethers may also be used.

Specific examples of the fluoroelastomers of this invention include, but are not limited to polymers having copolymerized units of the fluorovinyl ether cure site monomers of this invention and units of $VF_2$/HFP; $VF_2$/HFP/TFE; $VF_2$/PMVE; $VF_2$/PMVE/TFE; TFE/P; TFE/P/$VF_2$; and E/TFE/PMVE.

The cure site monomers useful in the fluoroelastomers of this invention are a class of fluorovinyl ethers having the general formula $CF_3CHFCF_2\!-\!(O)_n\!-\!(CH_2)_m\!-\!(CF_2)_p\!-\!R_f\!-\!OCF\!=\!CF_2$, wherein $R_f$ is a $C_{1-C8}$ perfluoroalkyl group or a $C_1\!-\!C_8$ perfluoroalkoxy group, n is 0 or 1, m is an integer from 1 to 3, and p is an integer from 1 to 4. Preferably $R_f$ is $-[OCF(CF_3)CF_2]_x\!-\!$, wherein x is 1 or 2; n is 1, m is 1 and p is an integer from 1 to 4. A specific example of these fluorovinyl ethers includes, but is not limited to $CF_3CHFCF_2\!-\!O\!-\!CH_2CF_2CF_2\!-\!O\!-\!CF(CF_3)CF_2\!-\!OCF\!=\!CF_2$.

These cure site monomers polymerize into the fluoroelastomer polymer chain through their vinyl group, resulting in copolymerized units having pendant $CF_3CHFCF_2\!-\!(O)_n\!-\!(CH_2)_m\!-\!(CF_2)_p\!-\!R_f\!-\!O\!-\!$ side chains. During curing, the side chains may readily dehydrofluorinate to form carbon-carbon double bonds. These sites of unsaturation then act as cure sites for crosslinking.

A particular characteristic of the cure site monomer of this invention is that it acts as an independent cure site monomer that takes part in crosslinking reactions with polyhydroxylic curing agents. That is, polymers that contain copolymerized units of this cure site monomer do not require the presence of copolymerized $VF_2$ monomer sequences flanked by perfluoromonomers (e.g. HFP/$VF_2$/HFP) for initiation of dehydrofluorination.

Because of the ease of hydrogen abstraction in the fluoroelastomer copolymers of this invention, the copolymers need contain only low levels of cure site monomer, i.e. 0.3–5 wt. % (preferably 0.7–3 wt. %), to promote efficient polyhydroxylic cures. This permits adjustment of other comonomer levels to maximize particular physical properties. Thus, the polymers of the present invention exhibit excellent cure characteristics when only low levels of cure site monomer are present.

The fluorovinyl ether monomers of this invention may be prepared by a process comprising the steps of a) chlorinating an hydroxy vinyl ether compound of the formula $HO\!-\!(CH_2)_m\!-\!(CF_2)_p\!-\!R_f\!-\!OCF\!=\!CF_2$ to produce a chlorinated hydroxy ether of the formula $HO\!-\!(CH_2)_m\!-\!(CF_2)_p\!-\!R_f\!-\!OCFCl\!-\!CF_2Cl$; b) condensing said chlorinated hydroxy ether with hexafluoropropene to produce a chlorinated ether of the formula $CF_3CHFCF_2\!-\!(O)_n\!-\!(CH_2)_m\!-\!(CF_2)_p\!-\!R_f\!-\!OCFCl\!-\!CF_2Cl$; and c) dechlorinating said chlorinated ether to produce a fluorinated vinyl ether of the formula $CF_3CHFCF_2\!-\!(O)_n\!-\!(CH_2)_m\!-\!(CF_2)_p\!-\!R_f\!-\!OCF\!=\!CF_2$. A preferred means for dechlorinating is by reaction with a reducing agent (such as zinc) in an aprotic solvent at a temperature between 70 to 140° C. The hydroxy vinyl ether starting material is known in the art. Some of these hydroxy vinyl ethers are available commercially from DuPont, or they may be synthesized by the process disclosed in U.S. Pat. No. 4,982,009.

In the above process, the hydroxy vinyl ether may be chlorinated by a variety of means including by the reaction with neat chlorine at a temperature between −15 to 40° C., preferably 0 to 10° C.

The chlorinated hydroxy ether may be condensed with hexafluoropropene by a variety of means, including by the reaction at a temperature between −15 to 70° C. of hexafluoropropylene with the chlorinated vinyl ether contained in an anhydrous aprotic solvent and in the presence of a strong base. Suitable aprotic solvents include dimethylsufoxide and dimethylformamide. Suitable strong bases include potassium t-butoxide.

The polymers of this invention may be prepared using free radical batch or semi-batch, or continuous free radical emulsion polymerization processes. They may also be prepared by free radical suspension polymerization processes.

For example, if a continuous emulsion process is utilized, the polymers are generally prepared in a continuous stirred tank reactor. Polymerization temperatures may be in the range of 40° to 145° C., preferably 80° to 135° C. at pressures of 1 to 8 MPa. Residence times of 20 to 360 minutes are preferred. Free radical generation may be effected through use of a water-soluble initiator such as ammonium persulfate, either by thermal decomposition or by reaction with a reducing agent such as sodium sulfite. An inert surface-active agent such as ammonium perfluorooctanoate may be utilized to stabilize the dispersion, usually in conjunction with addition of a base such as sodium hydroxide or a buffer such as disodium phosphate to control pH in the range 3 to 7. Unreacted monomer is removed from the reactor effluent latex by vaporization at reduced pressure. Polymer is recovered from the stripped latex by coagulation. For example, coagulation may be effected by reducing latex pH to about 3 by addition of acid, then adding a salt solution, such as an aqueous solution of calcium nitrate, magnesium sulfate, or potassium aluminum sulfate, to the acidified latex. The polymer is separated from the serum, then washed with water and subsequently dried. After drying, the product may be cured.

Chain transfer agents may be used in the polymerization in order to control the molecular weight distribution of the resulting polymers. Examples of chain transfer agents include isopropanol; methyl ethyl ketone; ethyl acetate; diethyl malonate; isopentane; 1,3-diiodoperfluoropropane; 1,4-diiodoperfluorobutane; 1,6-diiodoperfluorohexane; 1,8-diiodoperfluorooctane; methylene iodide; trifluoromethyl iodide: perfluoro(isopropyl) iodide; and perfluoro(n-heptyl) iodide. Polymerization in the presence of iodine-containing chain transfer agents may result in a polymer with one or two iodine atoms per fluoroelastomer polymer chain, bound at the chain ends (see for example U.S. Pat. No. 4,243,770 and U.S. Pat. No. 4,361,678). Such polymers may have improved flow and processability compared to polymers made in the absence of a chain transfer agent. Generally, up to about 1 weight percent iodine chemically bound to fluoroelastomer chain ends will be incorporated into the polymer, preferably from 0.1–0.3 wt. %.

An embodiment of the present invention is a curable composition that comprises the above-described copolymers and a polyhydroxylic curing agent. The polymers of the invention are also curable with amines and amine derivatives (e.g. carbamates).

Any of the known aromatic polyhydroxylic crosslinking agents that require accelerators for satisfactory cure rates are suitable for use with the fluoroelastomers of the present invention. The crosslinking agent is usually added in amounts of from about 0.5–4 parts by weight per hundred parts by weight fluoroelastomer (phr), usually 1–2.5 phr. Preferred crosslinking agents are di- tri-, tetrahydroxybenzenes, naphthalenes, anthracenes and bisphenols of the formula

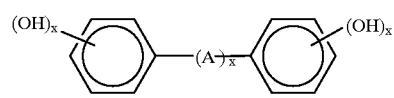

were A is a stable divalent radical, such as a difunctional aliphatic, cycloaliphatic, or aromatic radical of 1–13 carbon atoms, or a thio, oxy, carbonyl, sulfinyl, or sulfonyl radical; A is optionally substituted with at least one chlorine or fluorine atom; x is 0 or 1; n is 1 or 2 and any aromatic ring of the polyhydroxylic compound is optionally substituted with at least one atom of chlorine, fluorine, or bromine, a —CHO group, or a carboxyl or acyl radical (e.g. a —COR where R is OH or a $C_1$—$C_8$ alkyl, aryl, or cycloalkyl group). It will be understood from the above formula describing bisphenols that the —OH groups can be attached in any position (other than number one) in either ring. Blends of two or more such compounds can also be used.

Referring to the bisphenol formula shown in the previous paragraph, when A is alkylene, it can be, for example, methylene, ethylene, chloroethylene, fluoroethylene, difluoroethylene, 1,3-propylene, 1,2-propylene, tetramethylene, chlorotetramethylene, fluorotetramethylene, trifluorotetramethylene, 2-methyl-1,3-propylene, 2-methyl-1,2-propylene, pentamethylene, and hexamethylene. When A is alkylidene, it can be for example ethylidene, dichloroethylidene, difluoroethylidene, propylidene, isopropylidene, trifluoloisopropylidene, hexafluoroisopropylidene, butylidene, heptachlorobutylidene, heptafluorobutylidene, pentylidene, hexylidene, and 1,1-cyclohexylidene. When A is a cycloalkylene radical, it can be for example 1,4-cyclohexylene, 2-chloro-1,4-cyclohexylene, 2-fluoro-1,4-cyclohexylene, 1,3-cyclohexylene, cyclopentylene, chlorocyclopentylene, fluorocyclopentylene, and cycloheptylene. Further, A can be an arylene radical such as m-phenylene, p-phenylene, 2-chloro-1,4-phenylene, 2-fluoro-1,4-phenylene, o-phenylene, methylphenylene, dimethylphenylene, trimethylphenylene, tetramethylphenylene, 1,4-naphthylene, 3-fluoro-1,4-naphthylene, 5-chloro-1,4-naphthylene, 1,5-naphthylene, and 2,6-naphthylene. Bisphenol AF (4,4'-(hexafluoroisopropylidene)diphenol) is a preferred crosslinking agent.

Other useful crosslinlking agents include hydroquinonie, dihydroxybenzenes such as catechol, resorcinol, 2-methyl resorcinol, 5-methyl resorcinol, 2-methyl hydroquinone, 2,5-dimethyl hydroquinone; 2-t-butyl hydroquinone; and 1,5-dihydroxynaphthalene.

Additional polyhydroxy curing agents include alkali metal salts of bisphenol anions, quaternary ammonium salts of bisphenol anions and quaternary phosphonium salts of bisphenol anions. For example, the salts of bisphenol A and bisphenol AF. Specific examples include the disodium salt of bisphenol AF, the dipotassium salt of bisphenol AF, the monosodium monopotassium salt of bisphenol AF and the benzyltriphenylphosphonium salt of bisphenol AF. Quaternary ammonium and phosphonium salts of bisphenol anions and their preparation are discussed in U.S. Pat. Nos. 4,957,975 and 5,648,429.

In addition, derivatized polyhydroxy compounds, such as diesters, are useful crosslinking agents. Examples of such compositions include diesters of phenols, such as the diacetate of bisphenol AF, the diacetate of sulfonyl diphenol, and the diacetate of hydroquinone.

When cured with polyhydroxy compounds, the curable compositions will also generally include a cure accelerator. The most useful accelerators are quaternary phosphonium salts, quaternary alkylammonium salts, or tertiary sulfonium salts. Particularly preferred accelerators are n-tetrabutylammonium hydrogen sulfate, tributylallylphosphonium chloride and benzyltriphenylphosphonium chloride. Other useful accelerators include those described in U.S. Pat. Nos. 5,591,804; 4,912,171; 4,882,390; 4,259,463 and 4,250,278 such as tributylbenzylammonium chloride, tetrabutylammonium bromide, tetrabutylammonium chloride, benzyl tris(dimethylamino)phosphonium chloride; 8-benzyl-1,8-diazabicyclo[5,4,0]-7-undecenonium chloride, $[(C_6H_5)_2S^{30}(C_6H_{13})][Cl]^-$, and $[(C_6H_{13})_2S(C_6H_5)]^+[(CH_3CO_2)]^-$. In general, about 0.2 phr accelerator is an effective amount, and preferably about 0.35–1.5 phr is used.

If quaternary ammonium or phosphonium salts of bisphenols are used as curing agents, then addition of a cure accelerator is not necessary.

The polyhydroxy cure system will also contain a metal compound composed of a divalent metal oxide, such as magnesium oxide, zinc oxide, calcium oxide, or lead oxide, or a divalent metal hydroxide; or a mixture of the oxide and/or hydroxide with a metal salt of a weak acid, for example a mixture containing about 1–70 percent by weight of the metal salt. Among the useful metal salts of weak acids are barium, sodium, potassium, lead, and calcium stearates, benzoates, carbonates, oxalates, and phosphites. The amount of the metal compound added is generally about 1–15 phr, about 2–10 parts being preferred.

Other additives may be compounded into the fluoroelastomer to optimize various physical properties. Such additives include carbon black, stabilizers, plasticizers, lubricants, pigments, fillers, and processing aids typically utilized in perfluoroelastomer compounding. Any of these additives can be incorporated into the compositions of the present invention, provided the additive has adequate stability for the intended service conditions.

Carbon black is used in elastomers as a means to balance modulus, tensile strength, elongation, hardness, abrasion resistance, conductivity, and processability of the compositions. Carbon black is generally useful in amounts of from 5–60 phr.

In addition, or in the alternative, fluoropolymer fillers may be present in the composition. Generally from 1 to 50 phr of a fluoropolymer filler is used, and preferably at least about 5 phr is present. The fluoropolymer filler can be any finely divided, easily dispersed plastic fluoropolymer that is solid at the highest temperature utilized in fabrication and curing of the perfluoroelastomer composition. By solid, it is meant that the fluoroplastic, if partially crystalline, will have a crystalline melting temperature above the processing temperature(s) of the perfluoroelastomer(s). Such finely divided, easily dispersed fluoroplastics are commonly called micropowders or fluoroadditives. Micropowders are ordinarily partially crystalline polymers.

A preferred additive class includes molecular sieves, particularly zeolites. Molecular sieve zeolites are crystalline aluminosilicates of Group IA and Group IIA elements, such as sodium, potassium, magnesium, and calcium. Chemically, they are represented by the empirical formula: $M_{2/n}O.Al_2O_3.ySiO_2.wH_2O$ where y is 2 or greater, n is the cation valence, and w represents the water contained in the voids of the zeolite. Commercially available examples of such compositions include Molecular Sieve 3A, Molecular Sieve 4A, Molecular Sieve 5A, and Molecular Sieve 13X, all available from Aldrich Chemical Co., Inc. Milwaukee, Wis. Use of this class of additives prevents sponging and improves heat aging of vulcanizates upon press curing in many instances. In general, use of about 1–5 phr is sufficient.

Other preferred additives include modified silane coated mineral fillers. By "modified silane" is meant that the silane contains at least one reactive functional group such as an amino group, or an epoxy group. The mineral fillers used in this invention are preferably somewhat alkaline, such as calcium metasilicates ($CaSiO_3$), especially wollastonite. Wollastonite coated with either an aminosilane or an epoxysilane is especially preferred. These compounds are commercially available from Quarzwerke GmbH of Freschen, Germany as Tremin®283 EST (epoxysilane treated wollastonite) and Tremin®283 AST (aminosilane treated wollastonite). These modified silane coated mineral fillers prevent sponging of the fluoroelastomer composition during press cure and also accelerate the cure rate. Generally, about 5 to 80 phr modified silane coated mineral filler is useful in the compositions of this invention, about 10 to 60 phr being preferred.

The crosslinking agent, accelerator, metal oxide, and other additives are generally incorporated into the polymer by means of an internal mixer or on a rubber mill. The resultant composition is then cured, generally by means of heat and pressure, for example by compression transfer or injection molding.

The curable compositions of the present invention are useful in production of gaskets, tubing, seals and other molded components. Such articles are generally produced by molding a compounded formulation of the curable composition with various additives under pressure, curing the part, and then subjecting it to a post cure cycle. Depending on the monomers employed in the fluoroelastomer, the cured compositions have excellent low temperature flexibility and processability as well as excellent thermal stability and chemical resistance. They are particularly useful in applications such as seals and gaskets requiring a good combination of oil resistance, fuel resistance and low temperature flexibility, for example in fuel injection systems, fuel line connector systems and in other seals for high and low temperature automotive uses.

The invention is now illustrated by certain embodiments wherein all parts and percentages are by weight unless otherwise specified.

EXAMPLES

Test Methods

Cure Characteristics

Unless otherwise noted, cure characteristics were measured using an Alpha Technologies Ltd. 2000E moving disk rheometer (MDR), under conditions corresponding to ISO 6502 at a moving die frequency of 1.66 Hz, oscillation amplitude of ±0.50°, temperature of 180° C., sample size of 7–8 g, and the duration of the test was 12 minutes. The following cure parameters were recorded:

$M_H$: maximum torque level, in units of dN.m $M_L$: minimum torque level, in units of dN.m Delta M: difference between maximum and minimum torque, in units of dN.m $t_s2$: minutes to a 2.26 dNm rise above $M_L$ tc50: minutes to 50% of maximum torque tc90: minutes to 90% of maximum torque

Example 1

A monomer of the invention, 9,9,12-trihydro-perfluoro(3,6,10-trioxa-5-methyl-1-tridecene) [$CF_2$=CF—O—$CF_2$CF($CF_3$)O—$CF_2$—$CF_2$—$CH_2$O—$CF_2$CFHCF$_3$], was prepared by the following three step process.

In the first step, the chlorinated hydroxy ether intermediate 1,2-dichloro-9,9-dihydro-9-hydroxy-perfluoro (3,6-dioxa-5-methyl-nonane) [$CF_2$Cl—CFCl—O—$CF_2$CF($CF_3$)O—$CF_2$CF$_2$—$CH_2$OH] was prepared by chlorinating the hydroxy vinyl ether 9,9-dihydro-9-hydroxy-perfluoro(3,6-dioxa-5-methyl-1-nonene) [$CF_2$=CF—O—$CF_2$CF($CF_3$)O—$CF_2$CF$_2$—$CH_2$OH]. The preparation of this hydroxy vinyl ether is disclosed in U.S. Pat. No. 4,982,009. In this first step, 300 g (0.761 moles) of the hydroxy vinyl ether was cooled to a temperature between 0 and 10° C. and then chlorinated with neat chlorine. The progress of the reaction was monitored by gas chromatography. Chlorination was terminated when the majority of the hydroxy vinyl ether had been consumed. The resulting chlorinated hydroxy ether was purified by distillation, resulting in 200 g of a clear, colorless liquid having a boiling point of 100° C. at 25 mm Hg. NMR was used to positively identify the product: $^1$H-NMR (400 MHz, CDCl$_3$): δ4.00 (t, J=13.8 Hz, 2H), 1.94 (s, br, 1H); and $^{19}$F-NMR: (376.89 MHz, CDCl$_3$): −71.3 (m, 2F), −77.4 (m, 1F), −80.2 (t, 3F), −83.8 to −86.0 (m, 4F), −126.5 (t, 2F), −146.0 (m, 1F).

In the second step of the synthesis, the chlorinated hydroxy ether prepared in step 1 above, was condensed with hexafluoropropene to produce the chlorinated ether intermediate 1,2-dichloro-9,9,12-trihydro-perfluoro(3,6,10-trioxa-5-methyl-tridecane) [$CF_2$Cl—CFCl—O—$CF_2$CF($CF_3$)O—$CF_2$CF$_2$—$CH_2$O—$CF_2$CFHCF$_3$]. This was accomplished by charging a 400 ml stainless steel shaker tube with the 1,2-dichloro-9,9-dihydro-9-hydroxy-perfluoro-(3,6-dioxa-5-methyl-octane) (46.5 g, 0.1 mol) which was produced in step 1, potassium t-butoxide (1.58 g, 0.015 mol) and anhydrous dimethyl sulfoxide solvent (25 ml). The tube was then sealed, cooled and evacuated. Next, hexafluoropropene (30 g, 0.20 mol) was transferred into the tube. The tube was agitated for 8 hrs at 45° C. After cooling, the tube contents was distilled to give 45 g of 1,2-dichloro-9,9,12-trihydroperfluoro(3,6,10-trioxa-5-methyltridecane) as a clear, colorless liquid, having a boiling point of 99–100° C. at 27–28 mm Hg. Product identity was confirmed by NMR: $^1$H-NMR (400 MHz, CDCl$_3$): δ4.85 (dm, J=50 Hz, 2H), 4.35 (t, J=11.8 Hz, 1H); $^{19}$F-NMR: (376.89 MHz, CDCl$_3$): −71.4 (m, 2F), −77.4 (m, 1F), −76.0 (m, 3F). −80.3 (m, 3F), −80.5 to −85.0 (m, 6F), −124.1 (m, 2F), −145.9 (m, 1F), −212.5 (m, 1F).

In the third step, the choriniated ether intermediate produced in the second step was reduced to yield the fluorovinyl ether monomer of this invention. In this step, a reaction flask was charged with zinc-dust (23.5 g, 0.359 mol) in anhydrous dimethylformamide (DMF) solvent (180 ml). Bromine (1.5 ml) was then added to the flask in order to activate the zinc metal. The 1,2-dichloro-9,9,12-trihydro-perfluoro-(3,6,10-trioxa-5-methyl-1-tridecene (87 g, 0.141 mol) (produced above in the second step) was added and the reaction mixture was heated to a temperature between 98 and 104° C. for 4 hours. Gas chromatography indicated that the chorinated ether reactant was completely consumed. The reaction mixture was cooled and filtered to remove the zinc metal and zinc halide residues. The resulting two-layer liquid was separated, and the bottom layer was washed with water and distilled to give 42 g of the 9,9,12-trihydro-perfluoro-(3,6,10-trioxa-5-methyl-1-tridecene) monomer of this invention. The monomer was a clear, colorless liquid, having a boiling point of 88–89° C. at 41–42 mm Hg. This product was a diastereomer mixture. NMR confirmed the identity of the product: $^1$H-NMR (400 MHz, CDCl$_3$): [δ4.84 (dm, J=43.8 Hz, major isomer), 4.47 (dm, minor isomer), $^1$H total], 4.35(t, J=11.7 Hz, 2H); $^{19}$F-NMR: (376.89 MHz, CDCl$_3$): [−76.0 (m, major isomer), −68.2 (m, minor isomer), 3F total], −80.4 (m, 3F), −82.2 to 85.8 (m, 6F), −113.6 (m, 1F), −122.1 (4m, 1F), [−123.9 (m, major isomer), −124.2 (m, minor isomer), 2F total], −135.9 (4m, 1F), −145.5 (m, 1F), [−181.7(m), −188.6 (dm), −212.5 (m), 1F total]. IR (neat): 1840 cm$^{-1}$ ($CF_2$=CFO—).

Example 2

Fluoroelastomer polymer A of this invention (containing copolymerized units of VF$_2$/PMVE/TFE/CF$_2$=CF—O—CF$_2$CF(CF$_3$)O—CF$_2$CF$_2$—CH$_2$O—CF$_2$CFHCF$_3$) was prepared in the following manner.

A 4-liter polymerization vessel was charged with de-ionized water (2000 ml), disodium phosphate heptahydrate (20 g), ammonium perflutorooctanoate (38.9 g), and 9,9,12-trihydro-perfluoro(3,6,10-trioxa-5-methyl-1-tridecene) [CF$_2$=CF—O—CF$_2$CF(CF$_3$)O—CF$_2$CF$_2$—CH$_2$O—CF$_2$CFHCF$_3$] monomer (36 g). The reactor was sealed. Oxygen was removed from the reactor by evacuating it and then purging with nitrogen gas. The latter process was repeated three times. The reactor was then charged with a monomer gas mixture of TFE (10 g/hr), VF$_2$ (320 g/hr) and PMVE (670 g/hr) until the pressure had reached 200 psi (1.38 MPa) at 80° C. The reactor contents were stirred by a mechanical stirrer operating a 200 rpm. A solution of ammonium persulfate initiator (2.0 wt. % in water, 30 ml) was then added to the reactor at a rate of 10 ml/min. When a pressure drop (due to monomer consumption during the polymerization) was observed, the monomer gas feed was switched to a mixture of TFE (37 g/hr), VF$_2$ (212 g/hr) and PMVE (140 g/hr). The monomer feed flow rate was controlled so as to maintain the total reactor vessel pressure at 200 psi (1.38 MPa) as additional ammonium persulfate initiator solution was co-fed to the reactor at a rate of 0.2 ml/min. The polymerization was terminated after a total of 728 grams of monomer had been fed to the reactor. The resulting fluoroelastomer latex was then coagulated by addition of a magnesium sulfate aqueous solution. The coagulated fluoroelastomer polymer was collected by filtration, and washed thoroughly with warm water (70° C.). Polymer was then dried in an air oven at 80° C. The resulting fluoroelastomer polymer had a T$_g$ of −30.5° C., as determined by Differential Scanning Calorimetry (DSC). The composition of the polymer was analyzed by infrared spectroscopy and $^{19}$F-NMR (in hexafluorobenzene at 80° C.) and was determined to be 75.17 mol % VF$_2$, 6.30 mol % TFE, 18.44 mol % PMVE and 0.087 mol % 9,9,12-trihydroperfluoro(3,6,10-trioxa-5-methyl-1-tridecene). These mol % values correspond to 56.27 wt. %, 7.37 wt. %, 35.80 wt. % and 0.55 wt. %, respectively.

Example 3

Samples of polymer A from Example 2, and of a control polymer (a fluoroelastomer of the prior art containing 33.3 wt. % VF$_2$, 39.4 wt. % PMVE and 27.3 wt. % TFE) were compounded on a two-roll rubber mill with the components shown in Table I. Cure characteristics, measured according to the Test Method described above, are also reported in Table I.

The control polymer, which contained no cure site monomer, exhibited essentially no cure response, whereas polymer A of this invention cured well.

TABLE I

|  | Sample 1 | Control |
|---|---|---|
| Formulation |  |  |
| Polymer A | 100 |  |
| Control Polymer |  | 100 |
| Tremin ® 283 600EST[1] | 45 |  |
| MT Carbon Black[2] | 2.5 | 10 |
| Calcium Hydroxide[3] | 6 | 2 |
| MgO[4] | 3 | 2 |
| VPA No. 2[5] | 1 |  |
| TBAHS[6] | 0.5 | 1 |
| Bisphenol AF[7] | 2 | 2 |
| Cure Characteristics |  |  |
| $M_L$, dNm | 10.19 | — |
| $M_H$, dNm | 29.32 | — |
| Delta M, dNm | 19.13 | 0.6 |
| $t_s2$, minutes | 2.2 | — |
| tc50, minutes | 3.3 | — |
| tc90; minutes | 6.2 | — |

[1]Calcium meta-silicate treated with aminosilane (available from Quarzwerke GmbH, Freschen, Germany)
[2]Thermax FF N 990 medium thermal carbon black (available from Lehmann & Voss Co.)
[3]Rhenofit CF (available from Bayer)
[4]Elastomag ® 170 (available from Morton Performance Chemicals, Inc.)
[5]Rice Bran Wax (available from DuPont Dow Elastomers L.L.C.)
[6]Tetrabutylammonium hydrogen sulfate (available from DuPont Dow Elastomers L.L.C.)
[7]4,4'-(Hexafluoroisopropylidene)diphenol (available from DuPont Dow Elastomers L.L.C.)

What is claimed is:

1. A curable composition comprising:
   A. a fluoroelastomer comprising copolymerized units of a first monomer, said first monomer being a fluoroolefin selected from the group consisting of vinylidene fluoride and tetrafluoroethylene; copolymerized units of a second monomer, different from said first monomer, said second monomer selected from the group consisting of i) fluoroolefins, ii) hydrocarbon olefins, iii) perfluoro(alkyl vinyl)ethers and iv) perfluoro(alkoxy vinyl) ethers; and copolymerized units of a fluorinated vinyl ether cure site monomer of the formula $CF_3CHFCF_2-(O)_n-(CH_2)_m-(CF_2)_p-R_f-OCF=CF_2$, wherein $R_f$ is a $C_1-C_8$ perfluoroalkyl group or a $C_1-C_8$ perfluoroalkoxy group, n is 0 or 1, m is an integer from 1 to 3, and p is an integer from 1 to 4;
   B. a polyhydroxy crosslinking agent;
   C. a cure accelerator; and
   D. a metal oxide or metal hydroxide.

2. A curable composition of claim 1 wherein said first monomer in said fluoroelastomer is vinylidene fluoride and said second monomer is hexafluoropropylene.

3. A curable composition of claim 2 wherein said fluoroelastomer further comprises copolymerized units of tetrafluoroethylene.

4. A curable composition of claim 1 wherein said first monomer in said fluoroelastomer is vinylidene fluoride and said second monomer is perfluoro(methyl vinyl) ether.

5. A curable composition of claim 4 wherein said fluoroelastomer further comprises copolymerized units of tetrafluoroethylene.

6. A curable composition of claim 1 wherein said first monomer in said fluoroelastomer is tetrafluoroethylene and said second monomer is propylene.

7. A curable composition of claim 6 wherein said fluoroelastomer further comprises copolymerized units of vinylidene fluoride.

8. A curable composition of claim 1 wherein said first monomer in said fluoroelastomer is tetrafluoroethylene, said second monomer is ethylene and further comprising copolymerized units of perfluoro(methyl vinyl) ether.

9. A composition of claim 1 wherein the polyhydroxy crosslinking agent B is a crosslinking agent selected from the group consisting of i) dihydroxy-, trihydroxy-, and tetrahydroxy-benzenes, -naphthalenes, and -anthlacenes; ii) bisphenols of the formula

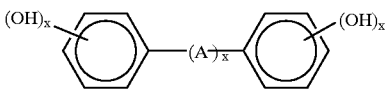

where A is a stable divalent radical; x is 0 or 1; and n is 1 or 2;
iii) dialkali salts of said bisphenols, iv) quaternary ammonium and phosphonium salts of said bisphenols, v) tertiary sulfonium salts of said bisphenols, and vi) esters of phenols.

10. A curable composition of claim 1 wherein said cure accelerator is selected from the group consisting of quaternary ammonium salts, tertiary sulfonium salts and quaternary phosphonium salts.

11. A curable composition of claim 1 wherein said cure accelerator C is selected from the group consisting of i) quaternary ammonium salts of the polyhydroxy crosslinking agent (B), ii) quaternary phosphonium salts of the polyhydroxy crosslinking agent (B) and iii) tertiary sulfonium salts of the polyhydroxy crosslinking agent.

* * * * *